United States Patent [19]

Adair

[11] 4,269,174
[45] May 26, 1981

[54] TRANSCUTANEOUS VASECTOMY APPARATUS AND METHOD

[75] Inventor: Edwin L. Adair, Littleton, Colo.

[73] Assignee: Medical Dynamics, Inc., Englewood, Colo.

[21] Appl. No.: 63,805

[22] Filed: Aug. 6, 1979

[51] Int. Cl.³ .............................................. A61B 19/00
[52] U.S. Cl. ................................ 128/1 R; 128/303.18
[58] Field of Search ............. 128/1 R, 303.18, 303.17, 128/303.14, 303.13, 303.1

[56] References Cited

U.S. PATENT DOCUMENTS

| | | |
|---|---|---|
| 1,919,543 | 7/1933 | Doane . |
| 3,598,108 | 8/1971 | Jamshidi ..................... 128/303.17 X |
| 3,628,524 | 12/1971 | Jamshidi .......................... 128/221 X |
| 3,630,192 | 12/1971 | Jamshidi ..................... 128/303.17 X |
| 3,698,394 | 10/1972 | Piper et al. ......................... 128/303.1 |
| 3,858,586 | 1/1975 | Lessen ................................ 128/303.1 |
| 3,886,944 | 6/1975 | Jamshidi ............................ 128/303.1 |

OTHER PUBLICATIONS

"An Electrocautery Instrument for the Fulguration of the Vas Deferens during Vasectomy for Sterilization", Instrument Society of America, May 1973, pp. 5-10, by Decker et al.
"Vascautery: Battery-Powered Instrument for Vasectomy", Urology, vol. III, May, 1974, pp. 604-605, by Schmidt et al.

*Primary Examiner*—John D. Yasko
*Attorney, Agent, or Firm*—Sheridan, Ross, Fields & McIntosh

[57] ABSTRACT

An apparatus and method is provided for initially anesthesizing the vas deferens of a male patient and then cauterizing the vas deferens to thereby permanently sterilize the male. In one embodiment, the apparatus includes a container to house an anesthetic fluid and which is removably attached to a first electrode. The first electrode includes a hollow needle having a tip formed at one end. The apparatus further includes a second electrode having a conducting probe with a distal end and which is slidably insertable through the hollow needle.

In operation, the needle is inserted through the scrotum wall and the tip positioned within the vas deferens. The anesthetic is forceably moved from the container through the hollow needle to desensitize the vas deferens. The container is removed from the first electrode and the second electrode is inserted into the first electrode. The distal end extends beyond the tip of the hollow needle and is positioned within the vas deferens. The first and second electrodes are connected to a source of power so that an electrical conducting path is formed between the two electrodes through the vas deferens to cauterize the vas deferens and thereby permanently sterilize the male patient.

In another embodiment, anesthetic may be injected with a conventional syringe and then the pointed electrodes inserted into the vas deferens and energized to complete the procedure. If desired, a unipolar electrode can be used in conjunction with a grounding plate. Also, the electrode can include a resistance heated needle tip for cauterizing the vas deferens. Finally, the electrodes may be arranged to provide two separate burn areas within the vas deferens to cauterize two separate areas.

23 Claims, 16 Drawing Figures

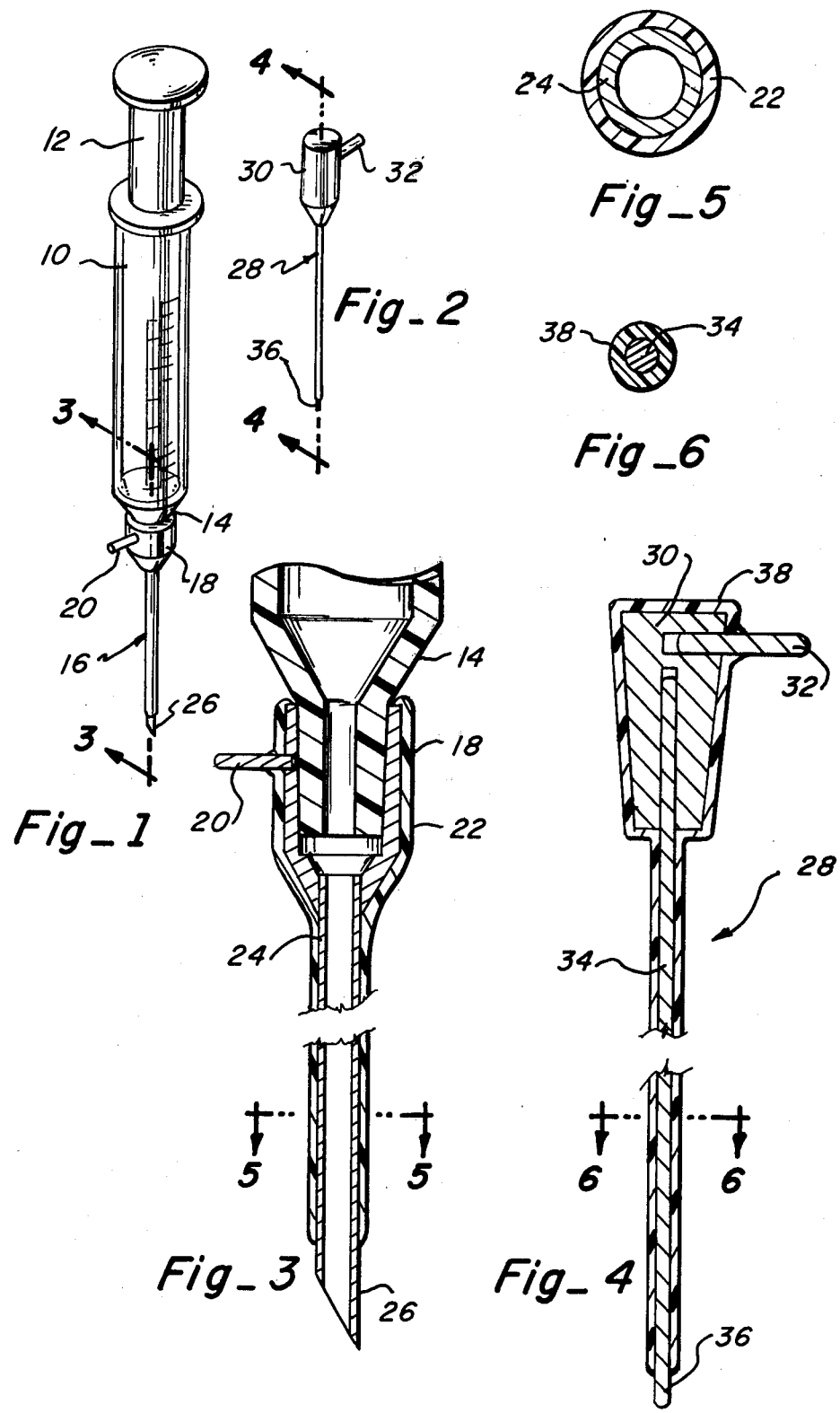

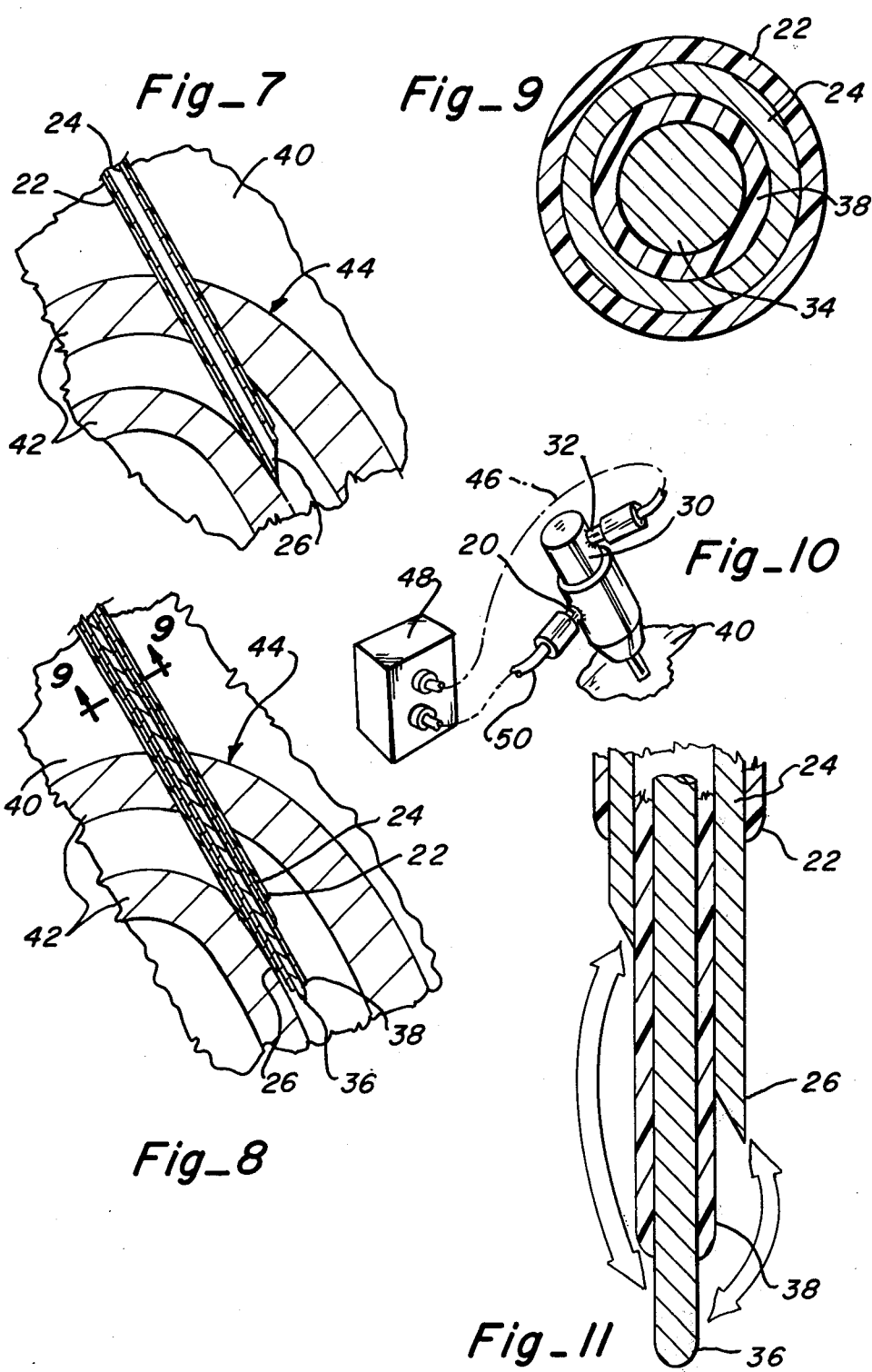

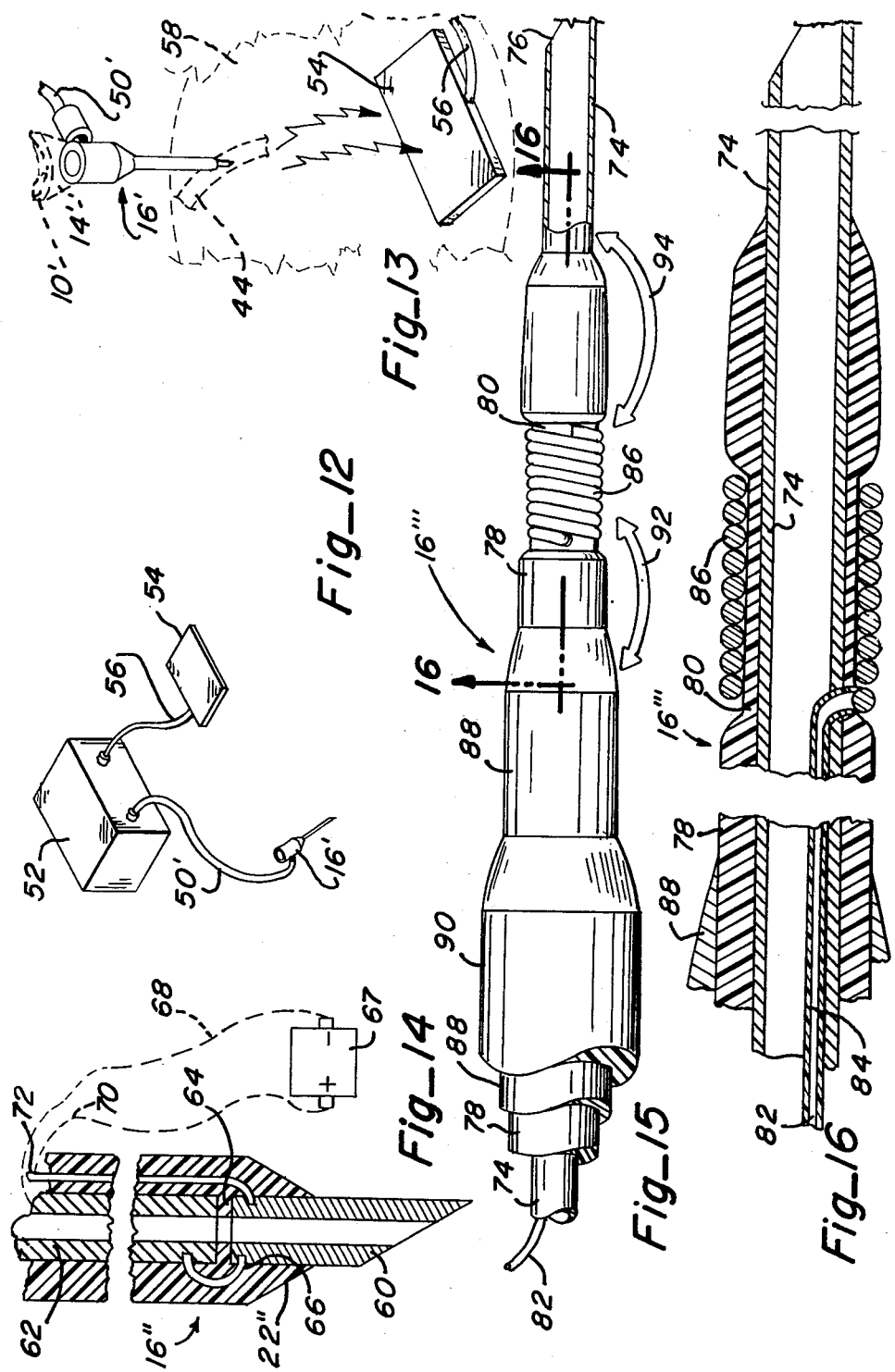

TRANSCUTANEOUS VASECTOMY APPARATUS AND METHOD

DESCRIPTION

1. Technical Field

This invention relates to an apparatus and a method for sterilizing a patient and, in particular, to a cauterizing instrument insertable through the scrotum and into the vas deferens to sterilize a male patient without making an incision in the scrotum wall.

2. Background Art

Generally, permanent sterilization of the male is accomplished by the surgical interruption of the vas deferens. The closure of the vas is provided either by ligation with surgical suture material or by cauterization. Each of these two methods requires a surgical opening of the scrotum. In addition, some form of anesthesia such as local anesthesia is provided. In a patient with a low threshold for pain or improperly prepared psychologically for the procedure, the vasectomy becomes difficult and time-consuming. Futhermore, complications of bleeding, hematoma formation, wound infection and sperm granuloma may result.

An apparatus which first requires an incision to be made in the scrotum is described in U.S. Pat. No. 4,103,688 to Edwards. In Edwards, a single, insulated electrode with a tip is disclosed. The tip is inserted into the opening of the severed end of a vas deferens to cauterize the end. Similarly, in U.S. Pat. No. 4,034,762 to Cosens, et al., an apparatus is illustrated having bipolar needle electrodes. An incision must be made prior to inserting the needle electrodes into the scrotum. A method and apparatus for sterilizing a female patient is described in U.S. Pat. No. 3,982,542 to Ford, et al. The sterilizing apparatus includes a tubular sheath and a stylet slidably inserted therein having a hook-shaped heating element. A hypodermic syringe needle having two electrodes is provided in U.S. Pat. No. 3,682,162. A sensory or motor nerve is initially identified and then medicament is injected as required.

DISCLOSURE OF INVENTION

In accordance with this invention, an apparatus and a method is provided for sterilizing a male human without an incision of the scrotum wall. The apparatus may also have application in the sterilization of female humans as well as in the sterilization of animals. In one form, the apparatus includes a container to house anesthesia and which is removably connected to a first electrode. The cauterizing element includes first electrode having a hollow needle insertable through the scrotum wall to deliver the anesthesizing substance to the vas deferens. After anesthesizing the vas deferens, the container is detached from the first electrode. A second electrode is slidably placed through the hollow needle. The second electrode includes a first or distal end which extends outwardly beyond the tip or bottom end of the first electrode. A source of power is connected between the first and second electrodes. The power source applies a high frequency current to the vas deferens to cauterize the tissue.

More particularly, the apparatus includes a container having a first end to receive a plunger. The container is generally cylindrical shaped to house an anesthesizing fluid. A second or converging end of the container is removably held in a first electrode. The first electrode includes a hollow needle connected to a hub. The hub is connected to a prong which extends in normal relation thereto. A tip or bevelled end is formed at the bottom portion of the first electrode. A first insulator surrounds the outer surface of the hub and portions of the hollow needle. The tip of the first electrode, however, is not surrounded by the first insulator. The apparatus further includes a second electrode having a support member with a conducting probe having one end held therein and a distal end extending outwardly therefrom. A connector member is held in the supporting member and is electrically connected thereto as is the conducting probe. A second insulator surrounds the outer surface of the supporting member and portions of the conducting probe which extend from the supporting member. The distal end of the probe, however, is not surrounded by the second insulator. In operation, the container is filled with an anesthetic fluid and connected to the first electrode. The needle is inserted through the scrotum wall and the tip thereof is positioned within the walls of the vas deferens. The plunger is moved to send the anesthestic through the needle tip to desensitize the vas deferens. After the vas deferens has been properly anesthesized, the container is removed from the first electrode. The second electrode is then inserted into the first electrode, but insulated therefrom. The conducting probe slidably moves through the hollow needle until the distal end extends therebeyond within the vas deferens. A power source is connected to the first and second electrodes so that a high frequency current is applied between the first and second electrodes through the vas deferens to cauterize the vas deferens and thereby close the same.

Alternatively, a grounding plate can be placed under a portion of the patient, such as his leg, and connected to ground, which then eliminates the need for the second electrode 28. In another embodiment, the tip of the needle may be heated resistively, as with a soldering iron, to burn or seer the vas deferens. Finally, the needle can be constructed so that the first electrode is between spaced portions of the second electrode so upon energization, two separate burn areas are provided in the vas deferens to improve the chances that the vas deferens will be completely cauterized and sealed to assure sterilization.

With each of these embodiments, it is possible to inject an anesthesic in the vas deferens with a traditional hypodermic needle and then insert the electrode seperately for carrying out the sterilization procedure. In this case, the needle and second electrode of the first embodiment could be formed as an integral unit and in the other embodiments, it would not be necessary for the needle to be hollow. Also, it should be understood that a cauterization element other than the above described electrodes may be used, such as a laser beam emitting device, ultrasonic or microwave probe, or a probe through which cryogenic fluid is passed.

Based on the foregoing, a number of advantages of the present invention are readily apparent. A unique apparatus and method is provided to initially anesthesize and then interrupt the vas deferens and thereby permanently sterilize a male patient. In a preferred embodiment, a hollow needle of this invention is inserted through the scrotum wall so a surgical incision need not be made. Consequently, complications of bleeding, hematoma formation, wound infection and sperm granuloma are greatly minimized. The container houses an anesthetic so that the vas deferens can be desensitized after insertion of the needle therewithin. Since the container is quickly and efficiently replaced by the second electrode while the needle remains in the vas deferens the needle need only be inserted through the scrotum wall one time. The fine, pointed distal end of the conducting probe extends beyond the tip of the needle so that the application of the cautery burn is precisely located while the remaining portions of the conducting probe are insulated. Furthermore, the conducting hollow needle is insulated from the conducting probe to assure an electrically safe apparatus. In another form of the invention, advantageously, a unipolar device may be used in conjunction with a grounding plate. Also, the device may take the form of a resistance heating device which seers the vas deferens or may be constructed to create two burn areas to increase the chances of complete cauterization of the vas deferens. Additional advantages of this invention will be apparent when taken in conjunction with the accompanying drawings.

BRIEF DESCRIPTION OF DRAWINGS

FIG. 1 is a perspective view of the container connected to the first electrode of this invention;

FIG. 2 is a perspective view of the second electrode of this invention;

FIG. 3 is an enlarged, fragmentary, longitudinal section, taken along line 3—3 of FIG. 1, showing details of the first electrode with the container connected thereto;

FIG. 4 is an enlarged, fragmentary, longitudinal section, taken along line 4—4 of FIG. 2, showing details of the second electrode;

FIG. 5 is a cross-sectional view of the first electrode;

FIG. 6 is a cross-sectional view of the second electrode;

FIG. 7 is a sectional view of the first electrode inserted through the scrotum wall with the arrows illustrating the movement of anesthesia from the needle to the vas deferens;

FIG. 8 is a sectional view showing the second electrode placed within the first electrode with the uninsulated pointed end of the conducting probe extending beyond the first electrode to the vas deferens;

FIG. 9 is a cross-sectional view of the second electrode held within the first electrode, but insulated therefrom;

FIG. 10 is a perspective view showing the power source connected to the first and second electrodes while portions of the apparatus are inserted into the scrotum; and FIG. 11 is a fragmentary, sectional view illustrating the path of current between the first and second electrodes.

FIG. 12 is a perspective view of another form of the invention utilizing a grounding plate;

FIG. 13 is a fragmentary perspective view showing the device of FIG. 12 in use;

FIG. 14 is an enlarged fragmentary vertical section through a further alternative device which has a resistance heated tip;

FIG. 15 is a plan view of a still further embodiment of the invention which forms two burns in the vas deferens simultaneously; and FIG. 16 is an enlarged longitudinal section, taken along line 16—16 of FIG. 15, showing details of the electrical connection.

BEST MODE FOR CARRYING OUT THE INVENTION

In accordance with one form of this invention, a container 10 is provided, as seen in FIG. 1, to house an anesthesizing fluid and includes a first or upper end through which a plunger 12 is inserted. The container 10 is generally a cylindrical-shaped tube which converges to a second or lower end 14. Container 10 is removably attached to a first electrode 16. First electrode 16 includes a hub portion 18. The lower end 14 of container 10 is removably held and surrounded by hub portion 18, as best seen in FIG. 3. A prong 20 extends outwardly from a side of the hub portion 18 in a generally perpendicular direction while being connected thereto. A first insulator 22 surrounds the outer surface of the hub portion 18, as shown in FIG. 5, to electrically insulate the hub portion 18 for reasons to be explained in detail later. First insulator 22 is typically formed from a synthetic fluorine-containing resin which provides adequate insulating properties and is available under the trademark "Teflon". A conducting hollow needle 24 is connected to hub portion 18 at a first end of needle 24 while a tip or bevelled end 26 is formed at the opposite end of hollow needle 24. First insulator 22 also extends around the outer surface of hollow needle 24 up to the point where tip 26 begins so that tip 26 remains uninsulated. Usually, a five mil coating of insulation, such as Teflon, is provided around the hollow needle 24 to electrically shield the same. The outer diameter of hollow needle 24 is conveniently 0.038 inches. The length of tip 26 is generally about 1/16 of an inch and is sharpened similar to a hypodermic needle.

The apparatus of this invention further includes a second electrode 28, as depicted in FIGS. 2 and 4. The second electrode 28 and first electrode 16 together comprise a cauterizing element. The second electrode 28 includes a conducting support member 30 and a connector 32 which is connected to support member 30 and extends outwardly therefrom in a generally perpendicular direction. Second electrode 28 further includes a conducting probe 34 having a first end connected to the support member 30 and a second or distal end 36. Thus, there is an electrical conducting path through prong 20, support member 30, and conducting probe 34. Similar to the first electrode 16, the outer surface of second electrode 28 is coated with insulation, namely, second insulator 38 as shown in FIG. 6. Second insulator 38 covers support member 30 and conducting probe 34, but distal end 36 remains uninsulated, as illustrated in FIG. 4. Conducting probe 34 is, preferably, made of a single, continuously-formed, solid conducting metal and has a diameter of approximately 0.020 inches.

The procedure for providing a vasectomy is pictorially represented in FIGS. 7–10. Initially, container 10 having an anesthetic therein, is removably attached to the first electrode 16. Hollow needle 24 is inserted into the scrotum 40 of the male patient. The tip 26 is positioned between the walls 42 of the vas deferens 44 as illustrated in FIG. 7. The plunger 12 is moved to deliver the anesthesia through the hollow needle 24 to the vas deferens 44 to desensitize the vas 44. The hollow needle 24 is of a length so that the hub portion 18 and prong 20 are outside the scrotum 40 when the tip 26 is within the vas 44. After providing the anesthetic, the container 10 is removed from the first electrode 18 while the latter remains positioned in the vas 44. Subsequently, second electrode 28 is inserted into first electrode 16. Inasmuch as the conducting probe 34, together with second insulator 38, have an outer diameter less than the inner diameter of hollow needle 24, conducting probe 34 is slidably received into hollow needle 24. The support member 30 is of a shape to be removaly held in hub portion 18 while conducting probe 34 is of a length such that distal end 36 and portions of insulated conducting probe 34 extend outwardly beyond hollow needle 24.

From FIG. 9, it is seen that conducting probe 34 is electrically insulated from hollow needle 24 by second insulator 38. A first conducting lead 46 from a source 48 of electrical energy is connected to connector 32 while a second conducting lead 50 is connected to prong 20, as illustrated in FIG. 10. Typically, the power source provides high frequency current and the first and second conducting leads 46,50 are electrically insulated as well as prong 20 and connector 32 so that an electrically safe apparatus is provided for the operator thereof and the male patient.

FIG. 11 illustrates the path of electrical energy from power source 48. The electrical energy moves between first and second electrodes 16,28 and through the vas deferens 44 cauterizing the vas 44 thereby. The distal end 36 is not insulated while being insulated from tip 26 of first electrode 16 so that a significantly large conducting area is exposed to facilitate the cauterizing step. Similarly, the tip 26 has no insulation around its outer surface and a conducting path is provided between first and second electrodes 16,28 through the vas 44. In addition, the distal end 36 is pointed to enhance the capability of precisely positioning the distal end 36 in the vas deferens 44 prior to cauterization. After the vas deferens 44 is closed, the hollow needle 24 and conducting probe 34 are removed from the scrotum 40.

A unipolar electrode 16', which is identical to electrode 16, previously described, is connected by means of a conducting lead 50' to a power source 52. A grounding plate 54 is connected by a second conducting lead 56 to power source 52. In use, the grounding plate 54 is placed under a portion of the anatomy of the patient 58, as shown in FIG. 13, preferably, the patient's leg. Electrode 16' is then inserted through the scrotum into the vas deferens 44 and anesthetic is injected from container 10' as previously described. After the vas deferens has been anesthestisized, container 10' can be removed. However, with the embodiments of FIGS. 12 and 13, a second electrode is not needed since the grounding plate 54 is in place. It is now necessary only to apply current to the electrode which causes the vas deferens to be cauterized, as previously explained. After cauterization, electrode 16' can be removed and the procedure is complete.

A still further embodiment is shown in FIG. 14. In this embodiment, an electrode 16'' is provided which has a resistance heated tip 60 that extends from insulator 22' as shown. The tip 60 is separated from tubular electrode 62 by wall 64 of insulator 22'' which extends between the tipe and the distal end of conductor 62. Conductor 62 and tip 60 are connected by a conducting strap 66. A power source 67 is provided which is connected by one conducting lead 68 to conductor 62 and a second lead 70 is connected to a wire 72 running longitudinally to insulator 22'' to resistance heating tip 60. Thus, when the circuit is completed to power source 52, resistance heating tip 60 becomes hot enough in a very short time to seer or burn the vas deferens to cauterize the tissue and sterilize the patient.

A still further embodiment is shown in FIGS. 15 and 16 wherein an electrode 16''' which is adapted to provide a double burn area to cauterize the vas deferens in two places to further assure complete sealing thereof. In this regard, the device includes a central hollow tubular member 74 which has a sharpened end 76 for inserting it through the scrotum wall and into the vas deferens. Encircling the tubular member is an insulative coating 78 which has a section 80 of reduced cross section, as best seen in FIGS. 15 and 16. A conducting lead 82 extends through tubular member 74 and then through an opening in section 80 as clearly shown in FIG. 16. Conducting lead 82 is coated with an insulative coating 84 along that portion which extends within tubular member 74, the insulation terminating as lead 82 passes through the opening in section 80. The lead 82 in then wrapped around section 80 to form a coil 86, the terminal end of the lead being attached to the outer surface of section 80 in any suitable manner. Advantageously, the difference in diameter of reduced section 80 and insulative coating 78 is approximately equal to the diameter of coil 86.

A larger metal tube or sleeve 88 extends around insulative coating 78 and therealong and is spaced a short distance from coil 86. In turn, metal tube 88 is encased in an insulative sleeve 90 which may be made of plastic material such as teflon.

In operation, the electrode device of FIGS. 15 and 16 must be inserted until at least tip 76, coil 86 and metal tube 88 are within the walls of the vas deferens. When in this position, the electrode may be energized resulting in current passing through the walls of the vas deferens between tip 76 and coil 86 as well as through the vas deferens between coil 86 and tube 88 thereby cauterizing the vas deferens in the areas between arrows 92 and 94 whereupon the device may be removed. By cauterizing the vas deferens at two locations instead of one, the chances of effecting a complete seal, and therefore sterilization, is greatly enhanced. It will be understood that if anesthetic is to be injected with a conventional hypodermic needle, then the tubular member 74 could be solid rather than hollow except for the space which accomodates conducting lead 82.

Although the foregoing discussion is concerned with the application of the apparatus of this invention in sterilizing a male human patient, it should be understood that other applications of the apparatus may be possible. The apparatus may be used in cauterizing body vessels other than the vas deferens. Additionally, the apparatus and method provided herein may have utility in sterilizing femal human patients and animals.

Based on the foregoing description, the advantages of this invention are readily discernable. An apparatus and method are provided for safely, quickly and efficiently sterilizing a male human patient. In one embodiment a cauterizing element includes a hollow needle having an uninsulated tip initially delivers anesthetic to the vas deferens so that it is desensitized. The hollow needle enables a second electrode to be inserted therethrough so that the uninsulated distal end of the second electrode extends therebeyond. The needle remains within the vas while the second electrode is connected thereto. A source of energy provides a cauterizing burn through the distal end to permanently close the vas. Complications of bleedings, hematoma formation, wound infection, and sperm granuloma are greatly minimized. Furthermore, the pointed distal end greatly facilitates the precise application of the cautery burn.

In a further embodiment, the unipolar device is used with a grounding plate under the patient to complete the circuit whereby upon energization, the vas deferens will be cauterized. In a still further embodiment, a resistively heated tip may be provided which burns or seers the vas deferens to seal it off. In still a further embodiment, a double burn area is provided wherein one electrode is in the form of a coil wrapped in insulative sleeve on a hollow tubular metal needle, the point of the needle being exposed so that upon energization of the circuit, one burn area is created between the coil and the tip of the needle. A second metal tubular member is positioned over the plastic sleeve and is spaced from the coil on the opposite side from the tip of the needle. Again, when the circuit is completed, a second burn area will be provided between the coil and the end of the metal tube cauterizing two portions of the vas deferens to further assure that sterilization is complete.

The invention has been described in detail with particular reference to a preferred embodiment thereof, but it will be understood that variations and modifications can be effected within the spirit and scope of the invention.

I claim:

1. An apparatus to cauterize a body vessel within the body of a patient without incising the patient's skin, said apparatus comprising:
   a first electrode including a conducting hollow needle having a tip insertable through the body of the patient and positionable adjacent the vessel; and
   a second electrode including a conducting probe having a distal end positioned and slidably received in said hollow needle, said distal end being positionable adjacent the vessel and electrically insulated from said first electrode so that a source of electrical energy is connectable to said first and second electrodes so that an electrical path is provided between said first and second electrodes through the vessel to cauterize and close the vessel.

2. The apparatus, as claimed in claim 1, wherein:
   said distal end of said conducting probe is generally pointed and extends beyond said tip of said hollow needle so that said distal end is positionable adjacent the body vessel to facilitate the cauterizing thereof.

3. The apparatus, as claimed in claim 1, further including:
   a first insulator surrounding portions of said hollow needle while said tip thereof remains free of said first insulator; and
   a second insulator surrounding portions of said conducting probe while said distal end thereof remains free of said second insulator.

4. An apparatus to anesthesize and cauterize the vas deferens thereby sterilizing the male patient without incising the patient's scrotum, said apparatus comprising:
   a removable containing means for holding an anesthetic;
   a cauterizing element connected to said containing means and including a conducting hollow needle having a tip insertable through the scrotum of the male and positionable between the walls of the vas deferens to inject the anesthetic from said removable containing means into the vas deferens to desensitize the vas deferens; and
   means for activating said cauterizing element for a selected period of time to cauterize and close the vas deferens and thereby sterilize the male patient.

5. An apparatus to anesthesize and cauterize the vas deferens thereby sterilizing the male patient without incising the patient's scrotum, said apparatus comprising:
   a removable containing means for holding an anesthetic;
   a first electrode removably connected to said containing means and including a conducting hollow needle having a tip insertable through the scrotum of the male and positionable between the walls of the vas deferens to inject the anesthetic from said removable containing means into the vas deferens to desensitize the vas deferens; and
   a second electrode in contact with the patient's body so that a source of electrical energy is connectable to said first and second electrodes to define an electrical path between said first and second electrodes through the vas deferens to cauterize and close the vas deferens and thereby sterilize the male patient.

6. The apparatus, as claimed in claim 5, wherein:
   said second electrode includes a conducting probe having a distal end, portions of said conducting probe being slidably, removably inserted into said hollow needle after removal of said containing means, said distal end being positionable within the walls of the vas deferens.

7. The apparatus, as claimed in claim 6, wherein:
   said distal end of said conducting probe extends beyond said tip of said hollow needle when said conducting probe is placed in said hollow needle so that said distal end is properly positionable within the vas deferens to facilitate the cauterizing thereof.

8. The apparatus, as claimed in claim 7, wherein:
   said conducting probe is a single, continuously formed, solid piece made of an electrical conducting metal; and
   said distal end of said conducting probe is generally pointed to further facilitate the cauterization.

9. The apparatus, as claimed in claim 5, wherein said second electrode includes:
   a grounding plate attachable to the patient's body.

10. The apparatus, as claimed in claim 6, wherein:
    the inner diameter of said conducting hollow needle is greater than the outer diameter of said conducting probe so that portions of said conducting probe are slidably inserted into said hollow needle.

11. The apparatus, as claimed in claim 6, further including:
    a first insulator surrounding portions of said hollow needle while said tip thereof remains free of said first insulator; and
    a second insulator surrounding portions of said conducting probe while said distal end thereof remains free of said second insulator.

12. An apparatus to provide a vasectomy for a male patient without incising the patient's scrotum, said apparatus comprising:
    a container to hold an anesthetic;
    a hub portion removably connectable to said container;
    a hollow needle connected to said hub portion and having a tip to pierce the wall of the scrotum and being positionable adjacent the vas deferens;

means connectable to said container to permit delivery of the anesthetic through said hollow needle to the vas deferens to desensitize the vas deferens;

a cauterizing element connectable to said hub portion after removal of said container, portions of said cauterizing element being slidably received within said hollow needle, said cauterizing element having a distal end to be positioned adjacent the vas deferens; and means for activating said cauterizing element for a selected period of time to cauterize and close the vas deferens, thereby sterilizing the male patient.

13. An apparatus to provide a vasectomy for a male patient without incising the patient's scrotum, said apparatus comprising:

a container to hold an anesthetic;

a hub portion removably connectable to said container;

a hollow needle connected to said hub portion and having a tip to pierce the wall of the scrotum and being positionable adjacent the vas deferens;

means connectable to said container to permit delivery of the anesthetic through said hollow needle to the vas deferens to desensitize the vas deferens;

a conducting probe being electrically insulated and connectable to said hub portion after removal of said container, portions of said conducting probe being slidably received within said hollow needle, said conducting probe having a distal end to be positioned adjacent the vas deferens so that a source of electrical energy is connectable to said hollow needle and said conducting probe to cauterize and close the vas deferens, thereby sterilizing the male patient.

14. The apparatus as claimed in claim 13, further including:

means for transmitting electrical energy to said hollow needle and said conducting probe.

15. The apparatus as claimed in claim 13, wherein:

said distal end is electrically uninsulated and extends beyond said tip of said hollow needle to facilitate the positioning thereof in the vas deferens prior to cauterizing the vas deferens.

16. An apparatus to anesthesize and cauterize the vas deferens thereby sterilizing a male patient without incising the patient's scrotum, said apparatus comprising:

a container to hold an anesthesizing fluid having a first end and a second end;

a plunger being connected to said first end of said container and slidable therewith;

a first electrode including a hub portion, a prong connected to said hub portion, and a hollow needle connected to said hub portion, said hub portion being removably connectable to said second end of said container while said hollow needle has a tip to pierce the scrotum wall and is insertable between the walls of the vas deferens so that the anesthesizing fluid exits said tip to desensitize the vas deferens upon activation of said plunger;

a first insulator surrounding said hub portion and portions of said hollow needle while said tip of said hollow needle remains free of said first insulator;

a second electrode including a support member, a connector connected to said support member, and a conducting probe having a distal end and connected to said support member, said support member being removably placed within said hub portion after removal of said container while portions of said conducting probe are slidably received within said hollow needle and said distal end extends beyond said tip of said hollow needle; and a second insulator surrounding said support member and portions of said conducting probe while said distal end of said conducting probe remains free of said second insulator so that when a source of electrical energy is connected between said first and second electrodes, a path for electrical energy is provided between said first and second electrodes through the vas deferens to cauterize the vas deferens.

17. An apparatus to anesthesize and cauterize the vas deferens thereby sterilizing a male patient without incising the patient's scrotum, said apparatus comprising:

removable containing means for holding an anesthetic;

a first electrode removably connected to said containing means and including a conducting hollow needle having a tip insertable through the scrotum of the male and positionable between the walls of the vas deferens to inject the anesthetic from said removable containing means into the vas deferens to desentisize the vas deferens; and a first insulator surrounding portions of said hollow needle while said tip of said hollow needle remains free of said first insulator;

a second electrode in the form of an uninsulated wire coil wrapped around said first insulator adjacent said needle tip;

a third electrode in the form of a sleeve surrounding a portion of said first insulator and having a distal end spaced from said second electrode and being in electrical contact with said first electrode;

a second insulator surrounding said third electrode while said distal end of said third electrode remains free of said second insulator, so that when a source of electrical energy is connected between said second electrode and said first and third electrodes, a path for electrical energy is provided between said second electrode and said first electrode and between said second electrode and said third electrode through the vas deferens to cauterize the vas deferens at two locations.

18. The apparatus as claimed in claim 17 wherein said first insulator includes:

a portion having a reduced diameter to receive said wire coil, the depth of said reduced portion being substantially equal to the diameter of the wire in said coil.

19. A method of closing the vas deferens to sterilize a male patient without incising the patient's scrotum, said method comprising the steps of:

inserting a needle into the scrotum of the male patient;

positioning said needle into the vas deferens;

injecting anesthetic into the vas deferens to desensitize the vas deferens;

activating a cauterizing element which includes at least said needle for a selected period of time to cauterize and thereby close the vas deferens to sterilize the male patient; and removal of said needle from the vas deferens and the scrotum.

20. A method of closing the vas deferens to sterilize a male patient without incising the patient's scrotum said method comprising the steps of:

inserting a hollow needle into the scrotum of the male patient with a container housing anesthetic attached to said hollow needle but positioned outside of the scrotum;

positioning said hollow needle into the vas deferens;

injecting the anesthetic into the vas deferens through said hollow needle to desensitize the vas deferens;

removing said container while said hollow needle remains in the scrotum;

slidably inserting a cauterizing element into said hollow needle;

activating the cauterizing element for a selected period of time to cauterize and thereby close the vas deferens to sterilize the male patient; and removing said hollow needle and cauterizing element from the vas deferens and the scrotum.

21. A method of closing the vas deferens to sterilize a male patient without incising the patient's scrotum, said method comprising the steps of:

inserting a needle into the scrotum of the male patient;

positioning said needle into the vas deferens;

injecting anesthetic into the vas deferens to desensitize the vas deferens;

applying electrical energy through a path which includes at least said needle and the vas deferens to cauterize and thereby close the vas deferens to sterilize the male patient; and removal of said needle from the vas deferens and the scrotum.

22. A method of closing the vas deferens to sterilize a male patient without incising the patient's scrotum, said method comprising the steps of:

inserting a hollow needle into the scrotum of the male patient with a container housing anesthetic attached to said hollow needle but positioned outside of the scrotum;

positioning said hollow needle into the vas deferens;

injecting the anesthetic into the vas deferens through said hollow needle to desensitize the vas deferens;

removing said container while said hollow needle remains in the scrotum;

slidably inserting a conducting probe into said hollow needle;

applying electrical energy through a path defined by said hollow needle, the vas deferens, and said conducting probe to cauterize and thereby close the vas deferens to sterilize the male patient; and removing said hollow needle and conducting probe from the vas deferens and the scrotum.

23. The method, as claimed in claim 22, wherein:

said conducting probe includes a distal end extending beyond said hollow needle to facilitate the location of said conducting probe in the vas deferens.

* * * * *